United States Patent
Jeong et al.

(10) Patent No.: US 12,221,596 B2
(45) Date of Patent: Feb. 11, 2025

(54) SKIN CHIP, METHOD FOR MANUFACTURING SKIN CHIP AND CELL SKIN CHIP, METHOD FOR MANUFACTURING SKIN CHIP AND CELL

(71) Applicant: INJE UNIVERSITY INDUSTRY—ACADEMIC COOPERATION FOUNDATION, Gimhae-si (KR)

(72) Inventors: Se Hoon Jeong, Gimhae-si (KR); Sung Tae Kim, Gimhae-si (KR)

(73) Assignee: INJE UNIVERSITY INDUSTRY-ACADEMIC COOPERATION FOUNDATION, Gimhae-si (KR)

( * ) Notice: Subject to any disclaimer, the term of this patent is extended or adjusted under 35 U.S.C. 154(b) by 935 days.

(21) Appl. No.: 17/268,383

(22) PCT Filed: Dec. 4, 2020

(86) PCT No.: PCT/KR2020/017608
§ 371 (c)(1),
(2) Date: Feb. 12, 2021

(87) PCT Pub. No.: WO2021/137455
PCT Pub. Date: Jul. 8, 2021

(65) Prior Publication Data
US 2021/0380911 A1 Dec. 9, 2021

(30) Foreign Application Priority Data

Dec. 30, 2019 (KR) .................. 10-2019-0177833
Nov. 17, 2020 (KR) .................. 10-2020-0153602

(51) Int. Cl.
| | | |
|---|---|---|
| C12N 5/077 | (2010.01) | |
| C12M 1/00 | (2006.01) | |
| C12M 1/12 | (2006.01) | |
| C12M 1/34 | (2006.01) | |
| C12M 3/00 | (2006.01) | |
| C12M 3/06 | (2006.01) | |
| C12N 5/071 | (2010.01) | |

(52) U.S. Cl.
CPC ............ *C12M 21/08* (2013.01); *C12M 23/16* (2013.01); *C12M 23/20* (2013.01); *C12M 25/02* (2013.01); *C12M 29/00* (2013.01); *C12M 41/00* (2013.01); *C12N 5/0629* (2013.01); *C12N 5/0656* (2013.01); *C12N 5/0698* (2013.01); *C12N 2502/094* (2013.01); *C12N 2502/1323* (2013.01); *C12N 2533/30* (2013.01)

(58) Field of Classification Search
CPC ...... C12M 23/16; C12M 21/08; C12M 23/20; C12M 3/00; G01N 33/5082; G01N 33/4836; G01N 2500/10
USPC ........................................................ 435/402
See application file for complete search history.

(56) References Cited

FOREIGN PATENT DOCUMENTS

| KR | 10-2016-0056040 A | 5/2016 |
| KR | 10-2018-0040407 A | 4/2018 |
| KR | 10-2018-0084621 A | 7/2018 |
| KR | 10-2019-0084256 A | 7/2019 |

OTHER PUBLICATIONS

Lukacs, B., "Skin-on-a-Chip Device for Ex Vivo Monitoring of Transdermal Delivery of Drugs—Design, Fabrication, and Testing," et al., Pharmaceutics 11(9): 445. doi: 10.3390/pharmaceutics11090445. Published Sep. 2, 2019. (Year: 2019).*
Maoz et al. LaB Chip 2017, 17(2294), pp. 1-9.*

* cited by examiner

*Primary Examiner* — Robert B Mondesi
*Assistant Examiner* — Mohammad Y Meah
(74) *Attorney, Agent, or Firm* — NKL Law; Jae Youn Kim (57) ABSTRACT

A method for manufacturing a skin chip according to an exemplary embodiment of the present disclosure may include: a step of forming first and second PDMS layers disposed on both surfaces of a porous membrane and each having a microfluidic channel through which a culture medium is transferred to both surfaces of the porous membrane; a step of forming first and second MEA substrate layers disposed on the outer surfaces of the first and second PDMS layers, respectively, and having metal electrodes for measurement of TEER arranged at positions corresponding to the channels; and a step of forming first and second PMMA layers disposed on the outer surfaces of the first and second MEA substrate layers, respectively. In the method for manufacturing a skin chip according to in an exemplary embodiment of the present disclosure, the porous membrane may be made of a polycarbonate having pores of a predetermined size.

13 Claims, 8 Drawing Sheets

SKIN CHIP, METHOD FOR MANUFACTURING SKIN CHIP AND CELL SKIN CHIP, METHOD FOR MANUFACTURING SKIN CHIP AND CELL

TECHNICAL FIELD

The present disclosure relates to a skin chip, a method for manufacturing a skin chip and a method for culturing cells using the skin chip, and more particularly, to a skin chip having a 3D multi-layer equipped with a microfluidic channel and an electrode sensor and being applicable to various types of skin, a method for manufacturing a skin chip, and a method for culturing cells using the skin chip.

BACKGROUND ART

Human skin protects the body from various chemicals and biological actions such as cosmetics, detergents, ultraviolet rays, pathogens, environmental pollutants, and microorganisms by providing a physiological barrier. The increase in such chemicals and biological actions may induce various skin responses such as skin inflammation, itchiness, allergy, and even tumor.

Accordingly, there is an increasing demand for drugs that alleviate the toxicity of specific chemicals. To achieve this object, millions of animal experiments, particularly animal experiments using mice, have been conducted globally. However, the experiments and researches using animals have three critical limitations.

The first is the issues associated with ethics and regulation, the second is cost and time, and the last limitation is that there are significant differences between mouse and human skin in skin thickness, hair density, appendages, etc. In addition, mouse does not have sweat glands except for at the sole of its feet. Due to these differences, predictions based on animal experiments instead of clinical tests have low accuracy.

Indeed, according to Humane Society International, although 9 out of 10 candidate drugs were safe and effective in animal experiments, they were unsuccessful when applied to human, and the successful prediction rate of the animal experiment results in clinical tests was below 10%.

In addition to these limitations, the 2009 EU regulation on cosmetics prohibits all animal experiments starting from March 2013, and other advanced countries such as Japan, US, etc. also show similar trends. For these reasons, the necessity of an in-vitro system mimicking human skin as much as possible is strongly preferred as an alternative to the animal experiments.

Since a human skin-like structure was first reported in the early 1980s, various in-vitro skin models have been developed and commercialized. However, most models are static culture systems which mimic only the epidermis of human skin based on fibroblasts and keratinocytes.

Because human skin includes pores, immune cells, melanocytes, Merkel cell complexes, blood vessels, nerve fibers and multilayer structures, the complicated structure of human skin cannot be embodied with such simple structures.

Accordingly, researches in various fields such as clinical industries, academic circles, etc. are making efforts to develop an in-vitro skin model close to the actual skin, called a 'skin-on-a-chip (skin chip)'. The skin is largely composed of the epidermis which moisturizes and protects the skin and the dermis which accounts for most of the volume of the skin. The skin chip is a small chip on which human or animal skin cells are cultured and enables experimentation of chemicals under a condition which is identical or similar to the skin structure.

Various types of skin chips have been developed thus far. First, a pump-free microfluidic chip model is a skin chip model embodied on a vibration platform for testing of drugs using the skin chip, and enables recycling of a culture medium.

However, it is limited in that the advantage of dynamic culture is limited because a skin-like structure is not reconstructed immediately in the microfluidic system. Second, there is a microfluidics-based skin chip model which embodies the epidermis (keratinocytes), the dermis (fibroblasts) and the vein endothelial cell layer for establishing inflammation and edema models of skin. Although skin cells can be cultured directly on the microfluidic chip, this model does not reflect the 3-dimensional complexity of human skin.

In addition, since it is designed in a traditional way to hold a sufficient amount of cells for analysis of gene expression, a large amount of cells are required (110 μL, 90 μL and 173 μL for epidermal, dermal and endothelial cells, respectively). This is not cost-effective when considering the high price of human cells. Furthermore, there is a more advanced skin chip model wherein blood vessels are embodied.

However, it is limited in that permeability measurement is possible only at the center portion of the skin chip due to contraction of collagen-based endothelial tissue. Although a skin chip model with the epidermis formed and enhanced barrier function has been developed to overcome the limitation, a fiber-based endothelial tissue is cultured on a porous membrane and then keratinocytes (epidermis) are cultured thereon without being separated by another membrane.

It is limited in that cell permeability measurement is difficult and an electrode should be inserted for measurement of cellular resistance (TEER) because an electrode is not included in the model.

The above description of the background art is merely provided for understanding of the background of the present disclosure and it should not be understood that the above-described technologies are known to those skilled in the art

REFERENCES OF RELATED ART

Korean Patent Publication No. 10-2018-0040407.
Korean Patent Publication No. 10-2018-0084621.

DISCLOSURE

Technical Problem

The present disclosure is directed to providing a skin chip having a 3D multi-layer equipped with a microfluidic channel and an electrode sensor and being applicable to various types of skin, a method for manufacturing a skin chip and a method for culturing cells using the skin chip.

Technical Solution

A method for manufacturing a skin chip according to an exemplary embodiment of the present disclosure may include: a step of forming first and second PDMS layers disposed on both surfaces of a porous membrane and each having a microfluidic channel through which a culture medium is transferred to both surfaces of the porous membrane; a step of forming first and second MEA substrate layers disposed on the outer surfaces of the first and second PDMS layers, respectively, and having metal electrodes for measurement of TEER arranged at positions corresponding to the channels; and a step of forming first and second PMMA layers disposed on the outer surfaces of the first and second MEA substrate layers, respectively.

In the method for manufacturing a skin chip according to an exemplary embodiment of the present disclosure, the porous membrane may be made of a polycarbonate having pores of a predetermined size.

In the method for manufacturing a skin chip according to an exemplary embodiment of the present disclosure, the first and second PDMS layers may be prepared by mixing a silicone base and a curing agent at a predetermined ratio, coating the mixture on a base plate, drying the same at a predetermined temperature for a predetermined time, cutting the same and then forming a microfluidic channel.

In the method for manufacturing a skin chip according to an exemplary embodiment of the present disclosure, the silicone base may be a SYLGARD 184 silicone elastomer base, the curing agent may be a SYLGARD 184 silicone elastomer curing agent, the silicone base and the curing agent may be mixed at a ratio of 10:1, foams may be removed completely using a vacuum pressure, the base plate may be an acrylic plate, a coating layer of a predetermined thickness may be formed by conducting spin coating at a predetermined rpm for a predetermined time, the spin-coated coating layer may be dried at a predetermined temperature for a predetermined time, a microfluidic channel having a predetermined shape may be formed, and the PDMS layer may be formed by cutting to predetermined width and length.

In the method for manufacturing a skin chip according to an exemplary embodiment of the present disclosure, the first and second MEA substrate layers may be prepared by depositing an adhesion layer and an electrode layer on a polycarbonate and forming the metal electrode on the polycarbonate by removing a predetermined region thereof.

In the method for manufacturing a skin chip according to an exemplary embodiment of the present disclosure, the adhesion layer may be formed from titanium, the metal electrode layer may be formed from gold foil, and the metal electrode may be formed by removing the predetermined region by photolithography or metal etching.

In the method for manufacturing a skin chip according to an exemplary embodiment of the present disclosure, a first channel formed in the first PDMS layer and a second channel formed in the second PDMS layer may cross each other with a predetermined tilt angle, and each of the first and second channels may be arranged in singular or plural numbers.

In the method for manufacturing a skin chip according to an exemplary embodiment of the present disclosure, the metal electrode formed on the first and second MEA substrate layers and the channel formed in the first and second PDMS layers may be formed at locations corresponding to each other.

The method for manufacturing a skin chip according to an exemplary embodiment of the present disclosure may further include a step of pressurizing at least two of the first and second PMMA layers, the first and second MEA substrate layers and the first and second PDMS layers using a pressurizing means.

The method for manufacturing a skin chip according to an exemplary embodiment of the present disclosure may further include a step of forming a through-hole through which the pressurizing means passes in the first and second PMMA layers, the first and second MEA substrate layers or the first and second PDMS layers.

The method for manufacturing a skin chip according to an exemplary embodiment of the present disclosure may further include a step of forming an injection port and a discharge port through which a liquid is injected or discharged in the first and second PMMA layers, the first and second MEA substrate layers or the first and second PDMS layers.

The method for manufacturing a skin chip according to an exemplary embodiment of the present disclosure may further include a step of drying the skin chip pressurized by the pressurizing means at a predetermined temperature for a predetermined time.

The method for manufacturing a skin chip according to an exemplary embodiment of the present disclosure may further include: a step of unleashing the pressurizing means after the skin chip has been pressurized and disposing a gasket between the first and second PMMA layers and the first and second MEA substrate layers; a step of sterilizing the skin chip in an autoclave and pressurizing the skin chip with the gasket disposed using the pressurizing means; and a step of connecting a tube to an injection port or a discharge port of the first and second PMMA layers.

A method for culturing cells using a skin chip manufactured by a method including: a step of forming first and second PDMS layers disposed on both surfaces of a porous membrane and each having a channel through which a culture medium is transferred to both surfaces of the porous membrane; a step of forming first and second MEA substrate layers disposed on the outer surfaces of the first and second PDMS layers, respectively, and having metal electrodes arranged at positions corresponding to the channels; and a step of forming first and second PMMA layers disposed on the outer surfaces of the first and second MEA substrate layers, respectively, which may include: a step of injecting a preservative to the porous membrane through the channel; a step of culturing cells for a predetermined period while injecting a keratinocyte culture medium of a predetermined concentration to the porous membrane through the channel; and a step of culturing the cells for a predetermined period while injecting a fibroblast culture medium of a predetermined concentration to the porous membrane through the channel.

A skin chip according to an exemplary embodiment of the present disclosure may include: first and second PDMS layers disposed on both surfaces of a porous membrane and each having a channel through which a culture medium is transferred to both surfaces of the porous membrane; first and second MEA substrate layers disposed on the outer surfaces of the first and second PDMS layers, respectively, and having metal electrodes for measurement of TEER arranged at positions corresponding to the channels; and first and second PMMA layers disposed on the outer surfaces of the first and second MEA substrate layers, respectively, wherein a first channel is formed in the first PDMS layer, a second channel is formed in the second PDMS layer, the first channel and the second channel are formed to be perpendicular to each other, a keratinocyte culture medium and a fibroblast culture medium can be injected through the first channel and the second channel, and skin cells are cultured as the keratinocyte culture medium and the fibroblast culture medium flow in directions perpendicular to each other.

Advantageous Effects

According to exemplary embodiments of the present disclosure, a skin chip (skin-on-a-chip, SOC) having a 3D multi-layer and being applicable to various types of skin has three or more multiple layers inside the chip in order to represent an environment similar to that of a living organism. Although the epidermis, the dermis and the endothelium are cultured on the respective layers, a structurally separated skin structure in which intercellular interactions are possible can be embodied because the porous membrane of each layer functions as a barrier.

In addition, the separated cell layers allow investigation of the permeability of chemicals into individual cells and the metal electrode located between the layers enables the measurement of TEER for all the cell layers.

In addition, the skin structure can be embodied more elaborately and measurement for a combination of two or more different types of cells is possible by increasing the number of the cell layer and the electrode layer to at least 2 or more.

In addition, by reducing the size of the chip such that only a small amount of cells/drug can be accommodated inside the chip, experiment can be conducted even with a small amount of expensive cells. The skin chip according to an exemplary embodiment of the present disclosure is applicable not only to human skin but also to the skin of other organs.

Furthermore, according to the present disclosure, the skin chip of the present disclosure is useful for testing of cosmetics, medications for external application to skin, toxicity substances, etc. since it represents a 3D structure close to the actual skin as compared to the existing stationary skin chips.

The effects of the present disclosure are not limited to those described above but may further include all effects that can be expected from the following detailed description and drawings.

BEST MODE

It is to be understood that the present disclosure is not limited by the specific exemplary embodiments described below but includes all changes, equivalents and substitutes included in the technical idea and scope of the present disclosure.

The terminology used in the present disclosure is for the purpose of describing specific exemplary embodiments only, and is not intended to limit the present disclosure. Unless the context clearly indicates otherwise, singular expressions can include plural expressions.

The terms "include", "have", etc. mean that there may be additional constitution, function, etc. in addition to the constitution, function, etc. specified in the present disclosure. The terms first, second, etc. are intended to distinguish one element from another, not to limit the elements.

Hereinafter, method for manufacturing a skin chip according to an exemplary embodiment of the present disclosure will be described in detail referring to the attached drawings.

Figure 1:
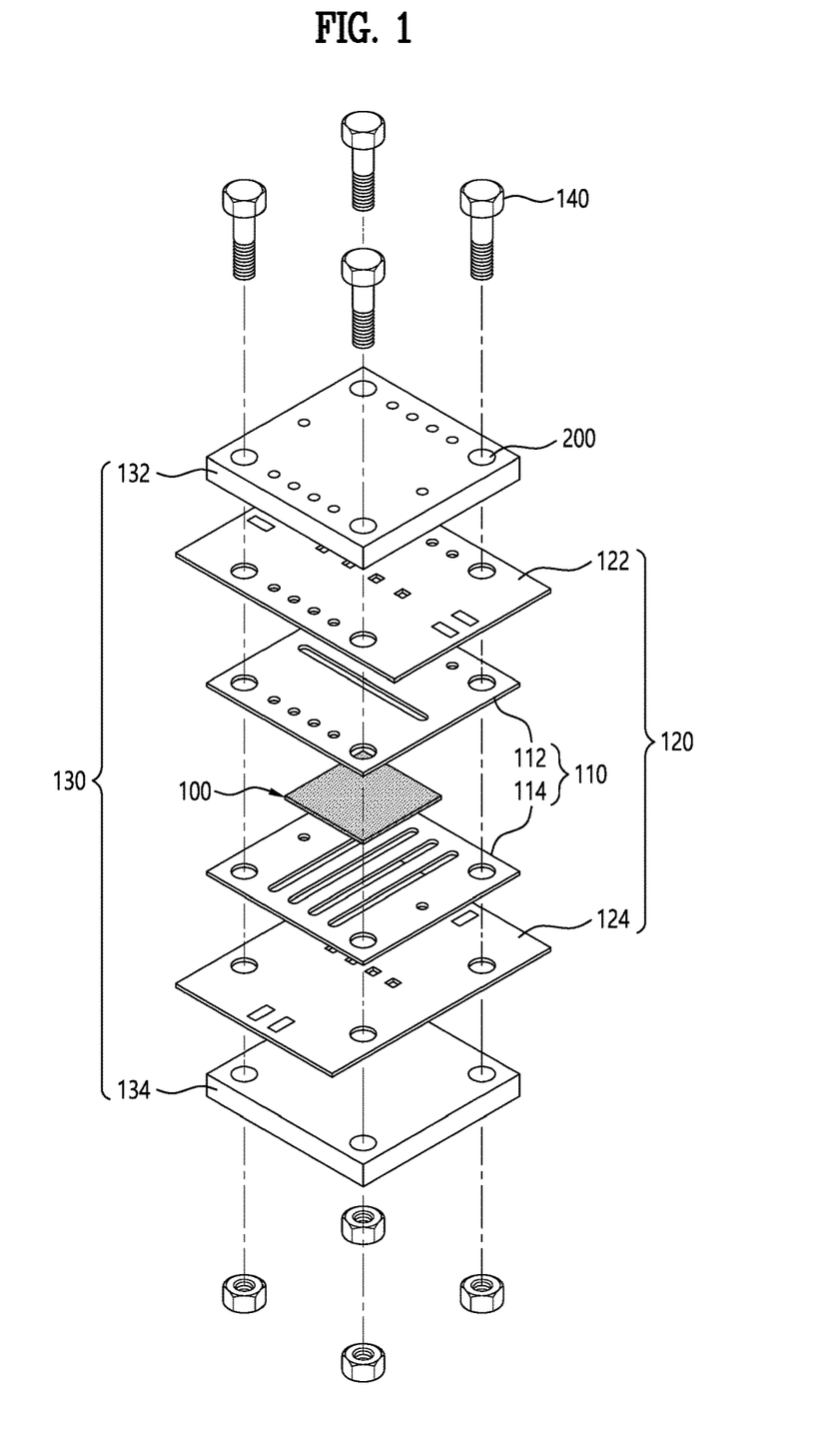
FIG. 1 is a schematic exploded perspective view of a 3D skin chip having a channel and a metal electrode according to an exemplary embodiment of the present disclosure.

FIG. 1 is a schematic exploded perspective view of a 3D skin chip having a channel and a metal electrode according to an exemplary embodiment of the present disclosure.

Referring to FIG. 1, the 3D skin chip includes a porous membrane 100, a PDMS (polydimethylsiloxane) layer 110, an MEA (microelectrode array) substrate layer 120, a PMMA (poly(methyl methacrylate)) layer 130 and a pressurizing means 140. The PDMS layer 110 includes a first PDMS layer 112 and a second PDMS layer 114, the MEA substrate layer 120 includes a first MEA substrate layer 122 and a second MEA substrate layer 124, and the PMMA layer 130 includes a first PMMA layer 132 and a second PMMA layer 134.

To describe in more detail, the porous membrane 100 made of a polycarbonate having pores with a size of 1 μm is disposed at the center, and the first and second PDMS layers 112, 114 having microfluidic channels are disposed above and below the porous membrane 100. The first and second PDMS layers 112, 114 are coupled with the first and second MEA substrate layers 122, 124 having metal electrodes capable of detecting electrical impedance.

In an exemplary embodiment of the present disclosure, in order to join these layers, the PMMA (poly(methyl methacrylate)) layer 130 with a thickness of 4 mm, which has an injection port, a discharge port and a screw hole, is located at the outermost side.

Figure 2:
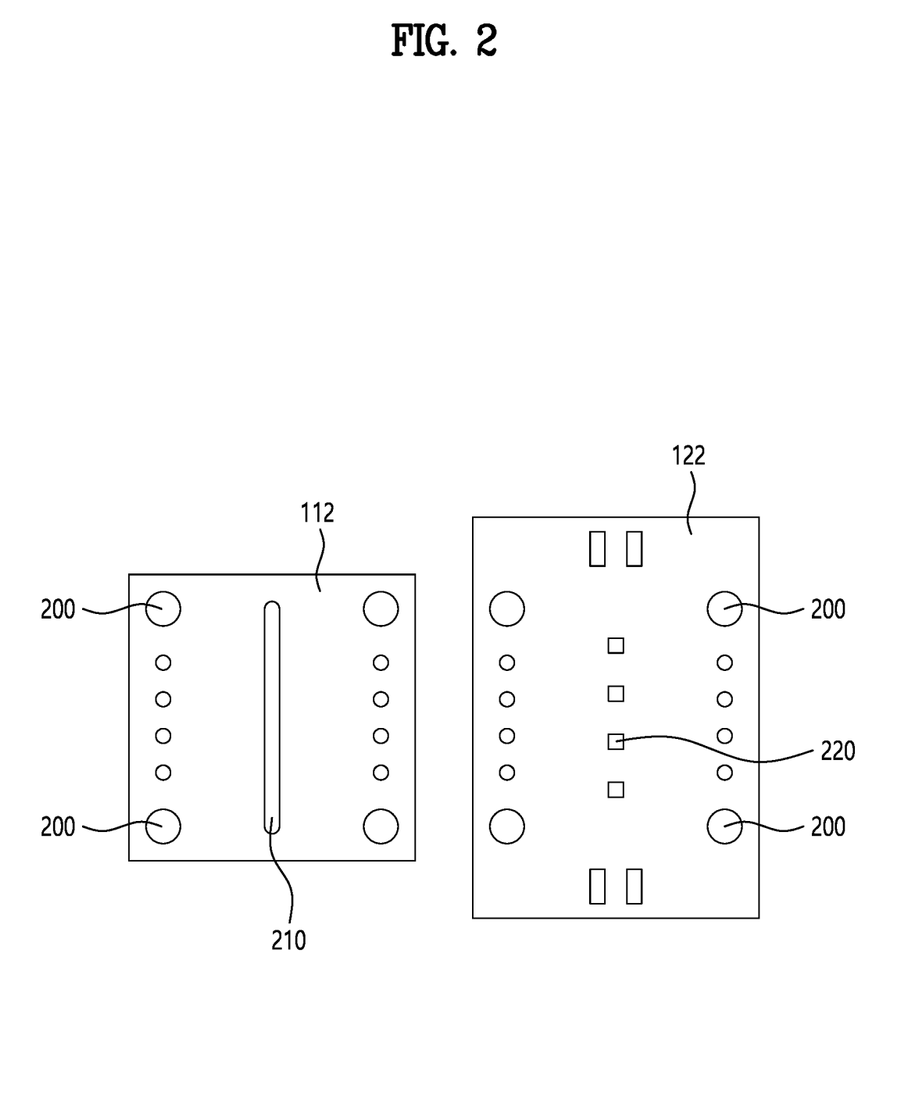
FIG. 2 is a plan view of a first PDMS layer with a channel formed and a first MEA substrate layer with a metal electrode formed according to an exemplary embodiment of the present disclosure.

FIG. 2 is a plan view of the first PDMS layer 112 with a channel formed and the first MEA substrate layer 122 with a metal electrode formed according to an exemplary embodiment of the present disclosure.

Referring to FIG. 2, the first PDMS layer 112 is attached to the upper surface of the porous membrane 100, the first MEA substrate layer 122 is attached to the upper surface of the first PDMS layer 112, a first channel 210 and a through-hole 200 through which a pressurizing means 140 such as a bolt penetrates is formed in the first PDMS layer 112, and a first metal electrode 220 and a through-hole 200 through which a pressurizing means 140 such as a bolt penetrates is formed in the first MEA substrate layer 122.

The first channel 210 formed in the first PDMS layer 112 may be formed to have a lengthy shape with predetermined width and length. One channel may be formed or two or more channels may be formed in parallel at predetermined intervals.

The first metal electrode 220 formed in the first MEA substrate layer 122 may be formed at a predetermined region corresponding to the first channel 210. One electrode may be formed or two or more electrodes may be formed in parallel at predetermined intervals.

Figure 3:
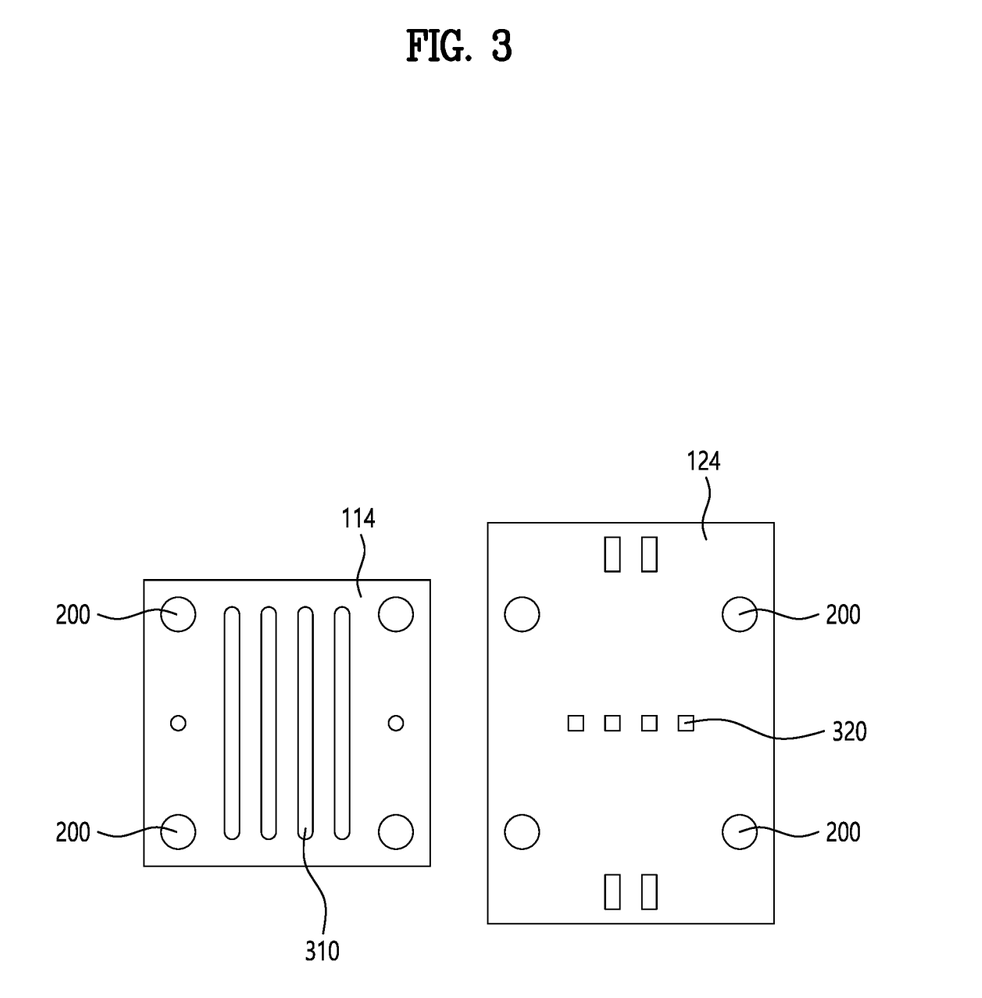
FIG. 3 is a plan view of a second PDMS layer with a channel formed and a second MEA substrate layer with a metal electrode formed according to an exemplary embodiment of the present disclosure.

FIG. 3 is a plan view of the second PDMS layer with a channel formed and the second MEA substrate layer with a metal electrode formed according to an exemplary embodiment of the present disclosure.

Referring to FIG. 3, the second PDMS layer 114 is attached to the lower surface of the porous membrane 100, the second MEA substrate layer 124 is attached to the lower surface of the second PDMS layer 114, a second channel 310 and a through-hole 200 through which a pressurizing means 140 such as a bolt penetrates is formed in the second PDMS layer 114, and a second metal electrode 320 and a through-hole 200 through which a pressurizing means 140 such as a bolt penetrates is formed in the second MEA substrate layer 124.

The second channel 310 formed in the second PDMS layer 114 may be formed to have a lengthy shape with predetermined width and length. One channel may be formed or two or more channels may be formed in parallel at predetermined intervals. Specifically, the second channel 310 may be formed to be perpendicular to the first channel 210.

The second metal electrode 320 formed in the second MEA substrate layer 124 may be formed at a predetermined region corresponding to the second channel 310. One electrode may be formed or two or more electrodes may be formed in parallel at predetermined intervals.

Figure 4:
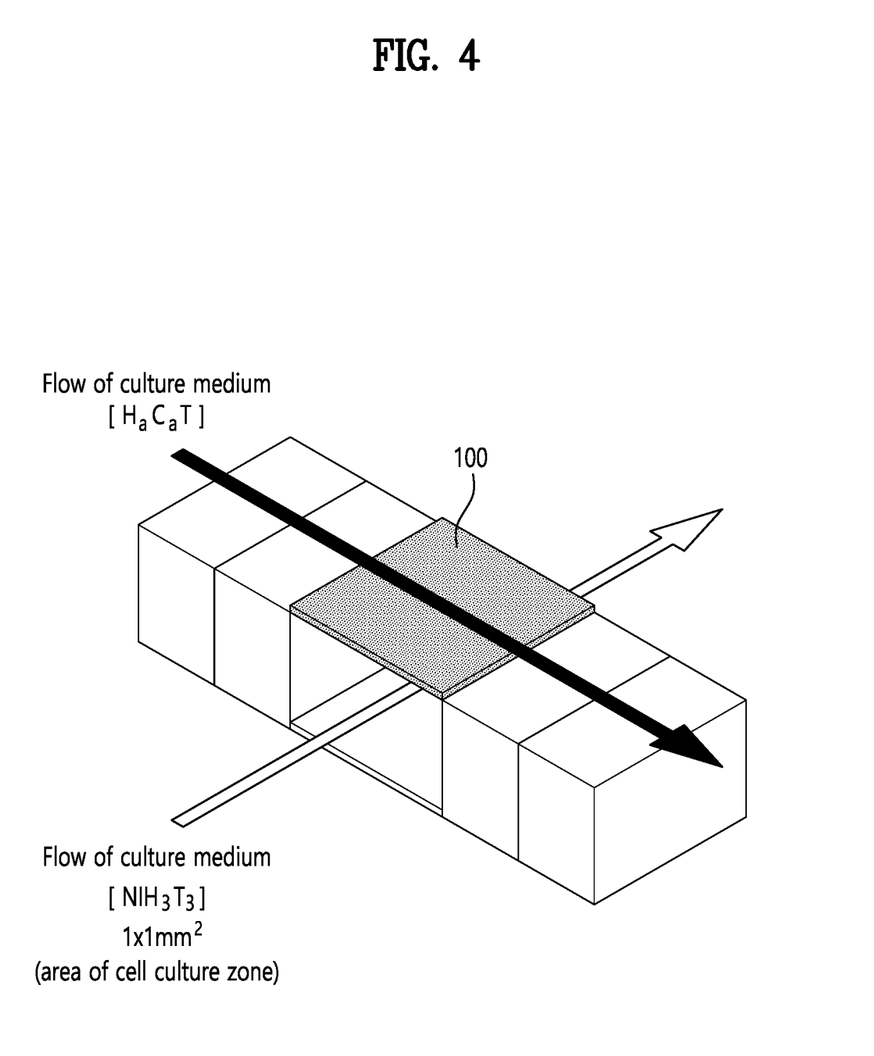
FIG. 4 is a schematic perspective view showing the flow of a culture medium through a porous membrane according to an exemplary embodiment of the present disclosure.

FIG. 4 is a schematic perspective view showing the flow of a culture medium through a porous membrane according to an exemplary embodiment of the present disclosure.

FIG. 4 schematically illustrates the flow of a culture medium and the culture of cells in a space formed by the porous membrane 100, the MEA substrate layer 120 and the microfluidic channel of the PDMS layer 110.

As shown in the figure, keratinocytes (HaCaT) are cultured as a culture medium (DMEM) flows in the direction of the arrow above the porous membrane 100, and fibroblasts (NIH3T3) are cultured as a culture medium (DMEM) flows in the direction of the arrow below the porous membrane 100.

Figure 5:
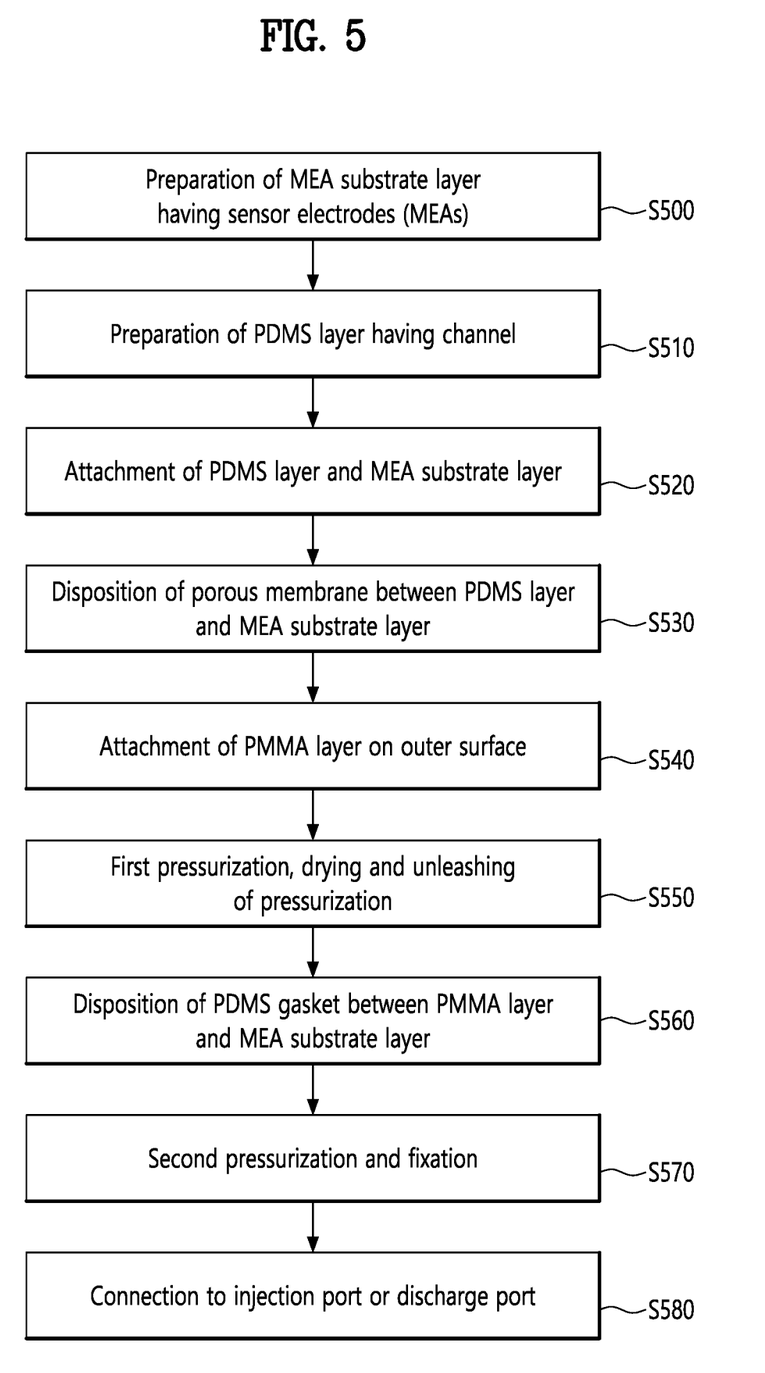
FIG. 5 is a flow chart illustrating a method for manufacturing a skin chip according to an exemplary embodiment of the present disclosure.

FIG. 5 is a flow chart illustrating a method for manufacturing a skin chip according to an exemplary embodiment of the present disclosure.

Referring to FIG. 5, in S500, an MEA substrate layer 120 having metal electrodes 220, 320 are formed. The MEA substrate layer 120 is prepared as follows. First, after sequentially depositing a thin titanium adhesion layer with a thickness of about 20 nm and a gold foil with a thickness of 200 nm on a polycarbonate, a MEA substrate layer 120 is formed by forming a metal electrode by photolithography and metal etching.

The metal electrodes (MEAs; metal electrode arrays) 220, 320 may be arranged as 1×4, 2×4, 3×4 or 4×4, and the exposed area of each of the metal electrodes 220, 320 may be about 1 mm². Then, after cutting the polycarbonate with the metal electrode deposited using a laser cutter (W, L: 24 mm, 28 mm), an injection port, a discharge port and a screw hole are formed.

In S510, a PDMS layer 110 having a microfluidic channel is formed. The PDMS layer 110 having a microfluidic channel is prepared as follows.

First, after sufficiently mixing a SYLGARD 184 silicone elastomer base and a SYLGARD 184 silicone elastomer curing agent at a ratio of 10:1 until foams completely cover the liquid and completely removing the foams using a vacuum tube, the mixture is poured onto an acrylic plate and then spin-coated using a spin coater at 130 rpm for 120 seconds to a thickness of 300 μm.

Then, the spin-coated PDMS is dried in a drying oven at 65° C. for 4 hours. After preparing a microfluidic channel (W, L, H: 1 mm, 19 mm, 300 μm) with a laser cutter, a PDMS layer 110 is completed by cutting to the same size as the MEA substrate layer 120 (W, L: 24 mm, 28 mm).

In S520, the PDMS layer 110 and the MEA substrate layer 120 with the metal electrode arranged are attached. Here, the first channel 210 of the PDMS layer 110 disposed above and the second channel 310 of the PDMS layer 110 disposed below are arranged to be perpendicular to each other. In S530, a porous membrane 100 made of a polycarbonate having pores with a size of about 1 μm is disposed between them.

In S540, two thick PMMA layers 130 (4 mm) are disposed on both surfaces to assemble a skin chip. In S550, after forming four pressurizing means 140 with uniform pressure using a torque wrench set to a predetermined pressure, the assembled skin chip is dried in a drying oven at 65° C. for 4 hours, so that the porous membrane 100 between the channels 210, 310 is dried. Then, the uppermost PMMA layer 130 is removed by unleashing the pressurizing means 140.

In S560, after disposing a PDMS GASKET between the MEA substrate layer 120 and the PMMA layer 130 and pressurizing again and fixing using the pressurizing means 140, the skin chip is sterilized in an autoclave and the pressurizing means 140 is fixed more tightly using the same torque wrench.

Finally, in S580, the skin chip assembly is completed by inserting tubes of an injection port and a discharge port into the PMMA layer 130 and fixing with an acrylic paste.

Figure 6:
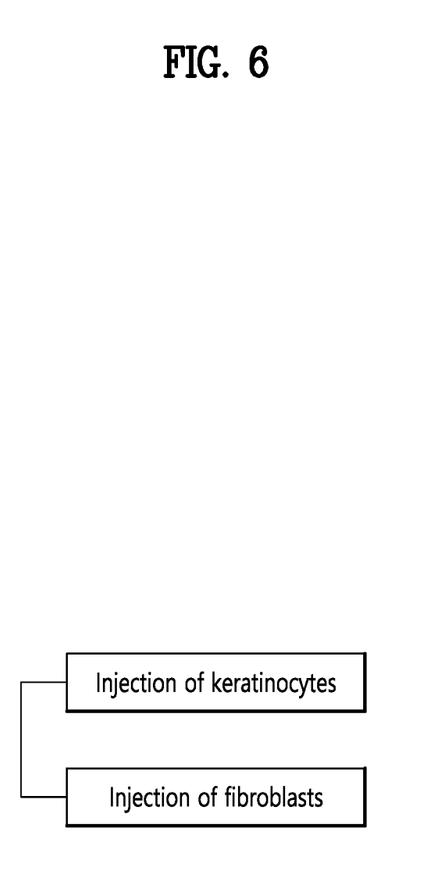
FIG. 6 shows the composition of culture components used in a skin chip according to an exemplary embodiment of the present disclosure.

FIG. 6 shows the composition of culture components used in a skin chip according to an exemplary embodiment of the present disclosure. Cells are cultured in the chip as follows.

Human-derived keratinocytes (HaCaT) are cultured in a DMEM culture medium (containing 10% (v/v) fetal bovine serum, 1% penicillin/streptomycin). The concentration of the keratinocytes is set to $1.0 \times 10^6$ cell/mL based on a 75 T flask. Mouse-derived fibroblasts (NIH3T3) are also cultured using the same culture medium. The concentration of the fibroblast is set to $3.0 \times 10^5$ cells/mL based on a 75 T flask.

The two types of cells are cultured under the condition of 37° C. and 5% $CO_2$. Subculturing is conducted when the cells fill about 80% or more of the flask surface. After removing the cell culture medium and washing the cells with DPBS, about 5 mL of 0.25% trypsin-0.53 mM EDTA is added and incubation is conducted under the condition of 37° C. 5% $CO_2$ for 5 minutes.

5 minutes later, after transferring the detached cells using a nutrient-free DMEM culture medium to a 15-mL tube and conducting centrifugation at 1500 rpm for 5 minutes, the supernatant is removed. Cell pellets with the supernatant removed are re-dispersed in 1 mL of DMEM containing fetal bovine serum and penicillin, and the re-dispersed cells are transferred to a fresh 75 T flask together with 15 mL of a culture medium.

Figure 7:
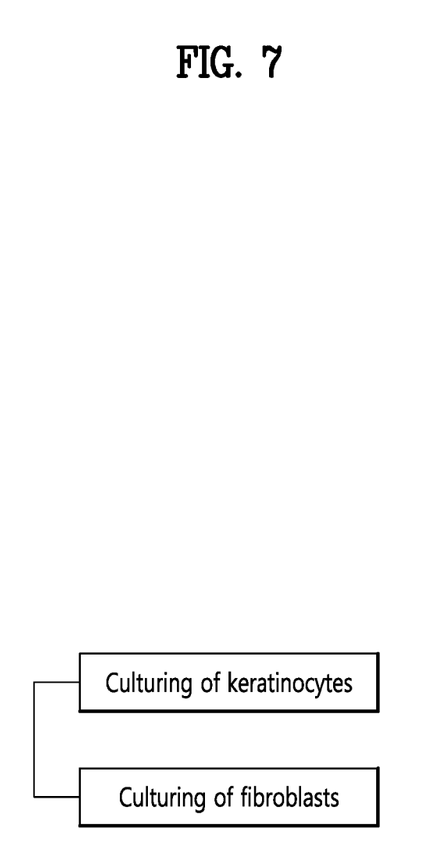
FIG. 7 shows the composition of culture components injected in a skin chip according to an exemplary embodiment of the present disclosure.

FIG. 7 shows the composition of culture components injected in a skin chip according to an exemplary embodiment of the present disclosure. Cells are cultured in the chip as follows.

In the skin chip according to an exemplary embodiment of the present disclosure, both surfaces of the porous membrane 100 made of a polycarbonate having pores with a size of about 1 μm are coated with poly-L-lysine.

Human-derived keratinocytes are injected through the microfluidic channels 210, 310 formed in the PDMS layer 110 at a concentration of 300 cells/mm² using a syringe, and then cultured at 37° C. in a 5% $CO_2$ incubator in a flow-free stationary state for about 24 hours in order to induce attachment and proliferation.

In order to remove unattached cells, the cells are cultured for 6 days while continuously flowing a fresh culture medium using a syringe pump at a flow rate of 0.1 μm/min.

Mouse-derived fibroblasts are injected into the microfluidic channels 210, 310 on the opposite surface of the polycarbonate membrane (i.e., the porous membrane 100) at the same concentration as the keratinocytes using a syringe, and then cultured in a flow-free state for 24 hours. After the attachment of the cells has been induced, the cells are cultured for 3 days while continuously flowing a fresh culture medium at a flow rate of 1.5 μm/min using a syringe pump.

In an exemplary embodiment of the present disclosure, cytotoxicity test is conducted as follows.

After seeding 100 μL of keratinocytes and fibroblasts onto a 96-well microplate, at concentrations of $1 \times 10^3$ cells/mL, respectively, and culturing in an incubator for 24 hours, the culture medium is replaced with a fresh culture medium.

Then, after diluting ibuprofen and ascorbic acid, which are substances to be used in skin permeability test, with a cell culture medium to appropriate concentrations and adding 10 μL each, the cells are cultured in an incubator for 24 hours. In addition, after adding 10 μL of a CCK reagent to each well 24 hours later, incubation is conducted for about 1-4 hours while measuring absorbance at a wavelength of 450 nm with 1-hour intervals.

Figure 8:
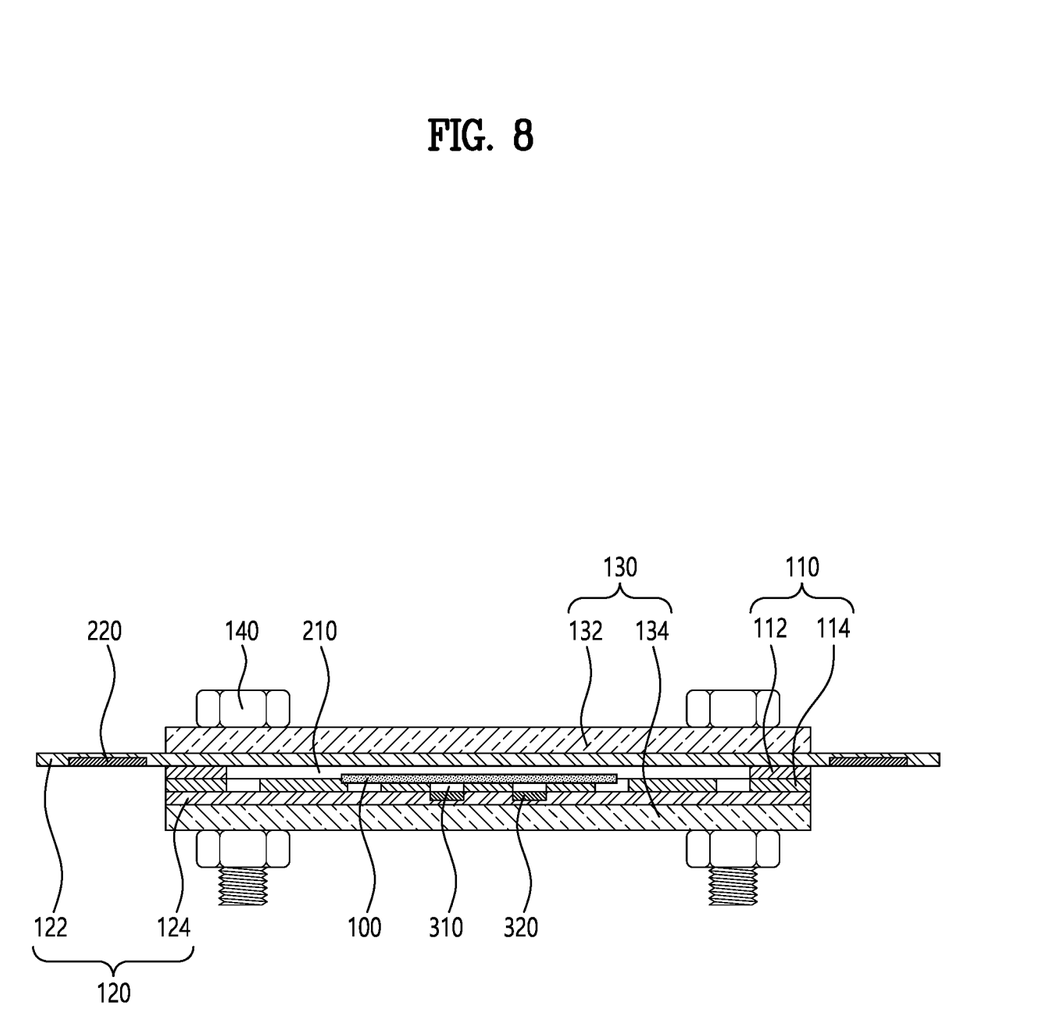
FIG. 8 is a cross-sectional view of a skin chip according to an exemplary embodiment of the present disclosure.

FIG. 8 is a cross-sectional view of the skin chip according to an exemplary embodiment of the present disclosure.

Referring to FIG. 8, in an exemplary embodiment of the present disclosure, the first PDMS layer 112, the first MEA substrate layer 122 and the first PMMA layer 132 are disposed sequentially above the porous membrane 100 made of a polycarbonate, and the second PDMS layer 114, the second MEA substrate layer 124 and the second PMMA layer 134 are disposed sequentially below the porous membrane 100.

The first channel 210 is formed in the first PDMS layer 112 and the second channel 310 is formed in the second PDMS layer 114. The channels are formed to be perpendicular to each other. A keratinocyte (HaCaT) culture medium and a fibroblast (NIH3T3) culture medium are injected through the first and second channels 210, 310 and skin cells are cultured as they flow in directions perpendicular to each other. Cellular resistance (transepithelial/transendothelial electrical resistance—TEER) can be measured effectively by the metal electrodes 220, 320.

As described above, the skin chip having the 3D multilayers, including the microfluidic channels 210, 310 and the metal electrodes 220, 320, is applicable to various types of skin and can represent an environment similar to that of a living organism.

In addition, although the epidermis, the dermis and the endothelium are cultured on the respective layers, a structurally separated skin structure in which intercellular interactions are possible can be embodied because the porous membrane 100 of each layer functions as a barrier, and the separated cell layers allow investigation of the permeability of chemicals into individual cells and the metal electrode located between the layers enables the measurement of cellular resistance for all the cell layers.

Furthermore, the skin chip of the present disclosure can be usefully used for testing of cosmetics, medications for external application to skin, toxicity substances, etc. since it represents a 3D structure close to the actual skin as compared to the existing stationary skin chips.

While the exemplary embodiments of the present disclosure have been described above, the technical idea of the present disclosure is not limited to the exemplary embodiments presented in the present disclosure. Those skilled in the art who understand the technical idea of the present disclosure will easily derive other exemplary embodiments through addition, change, deletion, etc. of constitutional elements within the technical idea of the present disclosure, which are also included within the scope of the present disclosure.

[Detailed Description of Main Elements]

| | |
|---|---|
| 100: porous membrane | 112: first PDMS layer |
| 114: second PDMS layer | 110: PDMS layer |
| 122: first MEA substrate layer | 124: second MEA substrate layer |
| 120: MEA substrate layer | 132: first PMMA layer |
| 134: second PMMA layer | 130: PMMA layer |
| 140: pressurizing means | 200: through-hole |
| 210: first channel | 220: first metal electrode |
| 310: second channel | 320: second metal electrode |

The invention claimed is:

1. A method for manufacturing a skin chip, the method comprising:
   forming first and second polydimethylsiloxane (PDMS) layers disposed on both surfaces of a porous membrane, each of the first and second PDMS layers having a microfluidic channel through which a culture medium is transferred to the both surfaces of the porous membrane, wherein the microfluidic channel of the first PDMS layer is a first channel and the microfluidic channel of the second PDMS layer is a second channel;
   forming first and second microelectrode array (MEA) substrate layers disposed on outer surfaces of the first and second PDMS layers, respectively, the first and second MEA substrate layers having metal electrodes for measuring cellular resistance arranged at positions corresponding to the microfluidic channels; and
   forming first and second poly (methyl methacrylate) (PMMA) layers disposed on outer surfaces of the first and second MEA substrate layers, respectively,
   wherein the first channel is formed on the first PDMS layer and the second channel is formed on the second PDMS layer, and the first and second channels are formed perpendicular to each other,
   wherein the first PDMS layer is attached to an upper surface of the porous membrane and has a through-hole through which the first channel and a pressurizing means are penetrated,
   wherein the second PDMS layer is attached to a lower surface of the porous membrane and has a through-hole through which the second channel and the pressurizing means are penetrated,
   wherein the metal electrodes include a first metal electrode and a second metal electrode,
   wherein the first MEA substrate layer is attached to an upper surface of the first PDMS layer to form a through-hole through which the first metal electrode and the pressurizing means are penetrated,
   wherein the first metal electrode is formed in a first region corresponding to the first channel,
   wherein the second MEA substrate layer is attached to a lower surface of the first PDMS layer to form a through-hole through which the second metal electrode and the pressurizing means are penetrated, and wherein the second metal electrode is formed in a second region corresponding to the second channel.

2. The method of claim 1, wherein the porous membrane is made of a polycarbonate having pores of a predetermined size.

3. The method of claim 1, wherein the forming the first and second PDMS layers comprises:
mixing a silicone base and a curing agent at a predetermined ratio;
coating the mixture on a base plate;
drying the coated base plate at a predetermined temperature for a predetermined time; and
cutting the dried coated base plate, and then forming the microfluidic channel.

4. The method of claim 3, wherein the silicone base is a SYLGARD 184 silicone elastomer base, the curing agent is a SYLGARD 184 silicone elastomer curing agent, the silicone base and the curing agent are mixed at the predetermined ratio of 10:1, and the base plate is an acrylic plate, and
wherein foams are removed completely using a vacuum pressure, a coating layer of a predetermined thickness is formed by conducting spin coating at a predetermined rpm for a predetermined time, the spin-coated coating layer is dried at the predetermined temperature for the predetermined time, the microfluidic channel having a predetermined shape is formed, and the first and second PDMS layers are formed by cutting to predetermined width and length.

5. The method of claim 1, wherein the forming the first and second MEA substrate layers comprises:
depositing an adhesion layer and a metal electrode layer on a polycarbonate; and
forming the metal electrode on the polycarbonate by removing a predetermined region thereof.

6. The method of to claim 5, wherein the adhesion layer is formed from titanium, the metal electrode is formed from gold foil, and the metal electrode is formed by removing the predetermined region by photolithography or metal etching.

7. The method of claim 1, wherein the first channel formed in the first PDMS layer and the second channel formed in the second PDMS layer cross each other at a predetermined tilt angle, and each of the first and second channels is arranged in singular or plural numbers.

8. The method of claim 1, wherein the metal electrodes formed on the first and second MEA substrate layers and the microfluidic channels formed in the first and second PDMS layers are formed at locations corresponding to each other.

9. The method of claim 1, further comprising pressurizing at least two of the first and second PMMA layers, the first and second MEA substrate layers, and the first and second PDMS layers using a pressurizing means.

10. The method of claim 9, further comprising forming the through-hole through which the pressurizing means passes in the first and second PMMA layers, the first and second MEA substrate layers, or the first and second PDMS layers.

11. The method of claim 10, further comprising forming an injection port and a discharge port through which a liquid is injected and discharged, respectively, in the first and second PMMA layers, the first and second MEA substrate layers, or the first and second PDMS layers.

12. The method of claim 9, further comprising drying the skin chip pressurized by the pressurizing means at a predetermined temperature for a predetermined time.

13. The method of claim 12, further comprising:
unleashing the pressurizing means after the skin chip has been pressurized and disposing a gasket between the first and second PMMA layers and the first and second MEA substrate layers;
sterilizing the skin chip in an autoclave and pressurizing the skin chip with the gasket disposed using the pressurizing means; and
connecting a tube to an injection port or a discharge port of the first and second PMMA layers.

* * * * *